(12) United States Patent
Lv et al.

(10) Patent No.: US 9,873,649 B2
(45) Date of Patent: Jan. 23, 2018

(54) PROCESS FOR THE JOINT PREPARATION OF 1,3,3,3-TETRAFLUOROPROPENE AND 2,3,3,3-TETRAFLUOROPROPENE

(71) Applicant: XI'AN MODERN CHEMISTRY RESEARCH INSTITUTE, Xi'an, Shaanxi (CN)

(72) Inventors: Jian Lv, Shaanxi (CN); Hui Ma, Shaanxi (CN); Bo Wang, Shaanxi (CN); Wei Zhang, Shaanxi (CN); Zhiqiang Yang, Shaanxi (CN); Yujie Gu, Shaanxi (CN); Wei Mao, Shaanxi (CN); Jijun Zeng, Shaanxi (CN); Xiaobo Tang, Shaanxi (CN); Zhenhua Zhang, Shaanxi (CN)

(73) Assignee: Xi'an Modern Chemistry Research Institute, Xi'an (CN)

( * ) Notice: Subject to any disclaimer, the term of this patent is extended or adjusted under 35 U.S.C. 154(b) by 0 days.

(21) Appl. No.: 15/535,260

(22) PCT Filed: Feb. 5, 2015

(86) PCT No.: PCT/CN2015/072304
§ 371 (c)(1),
(2) Date: Jun. 12, 2017

(87) PCT Pub. No.: WO2016/090744
PCT Pub. Date: Jun. 16, 2016

(65) Prior Publication Data
US 2017/0320797 A1    Nov. 9, 2017

(30) Foreign Application Priority Data

Dec. 13, 2014  (CN) .......................... 201410772521

(51) Int. Cl.
| | | |
|---|---|---|
| *C07C 17/20* | (2006.01) | |
| *C07C 17/21* | (2006.01) | |
| *C07C 17/23* | (2006.01) | |
| *C07C 17/383* | (2006.01) | |
| *B01J 37/26* | (2006.01) | |
| *B01J 37/08* | (2006.01) | |
| *B01J 23/745* | (2006.01) | |
| *B01J 37/03* | (2006.01) | |

(52) U.S. Cl.
CPC ............ *C07C 17/206* (2013.01); *B01J 23/745* (2013.01); *B01J 37/035* (2013.01); *B01J 37/08* (2013.01); *B01J 37/26* (2013.01); *C07C 17/21* (2013.01); *C07C 17/23* (2013.01); *C07C 17/383* (2013.01)

(58) Field of Classification Search
CPC ......... C07C 17/21; C07C 17/23; C07C 17/25; C07C 21/18; C07C 19/10; B01J 37/26; B01J 23/745; B01J 37/08; B01J 37/03
See application file for complete search history.

(56) References Cited

U.S. PATENT DOCUMENTS

| | | | | |
|---|---|---|---|---|
| 7,678,949 B2 * | 3/2010 | Rao | ........................ | B01J 23/868 570/156 |
| 8,546,623 B2 * | 10/2013 | Sharratt | .................. | C07B 39/00 570/155 |

* cited by examiner

*Primary Examiner* — Jafar Parsa
(74) *Attorney, Agent, or Firm* — Stites & Harbison, PLLC; David W. Nagle, Jr.; Terry L. Wright (57) ABSTRACT

A process for the joint preparation of 1,3,3,3-tetrafluoropropene and 2,3,3,3-tetrafluoropropene, comprising: (a) starting materials comprising at least one compound having the structure of formula I, II or III are reacted with hydrogen fluoride, producing 1,2,3-trichloro-3,3-difluoropropene, 1,2,3-trichloro-1,1,2-trifluoropropane, and 1,2,3-trichloro-1,1,3-trifluoropropane; in the compounds of said formulae $CF_{2-m}Cl_m$=CCl—$CHF_{2-n}Cl_n$ (Formula I), $CF_{3-p}Cl_p$CHCl=$CH_2$Cl (Formula II), and $CF_{3-x}Cl_xCF_{2-y}Cl_y$-$CHF_{2-z}Cl_z$ (Formula III), m=0, 1, 2; n=1, 2; p=2, 3; x=1, 2, 3; y=1, 2; z=1, 2 and 4≤x+y+z≤6; (b) the 1,2,3-trichloro-3,3-difluoropropene, 1,2,3-trichloro-1,1,2-trifluoropropane and 1,2,3-trichloro-1,1,3-trifluoropropane undergo dechlorination, producing 3-chloro-3,3-difluoropropyne, 3-chloro-2,3,3-trifluoropropene and 3-chloro-1,3,3-trifluoropropene; and (c) the 3-chloro-3,3-difluoropropyne, 3-chloro-2,3,3-trifluoropropene and 3-chloro-1,3,3-trifluoropropene are reacted with hydrogen fluoride, simultaneously yielding 1,3,3,3-tetrafluoropropene and 2,3,3,3-tetrafluoropropen.

12 Claims, 3 Drawing Sheets

PROCESS FOR THE JOINT PREPARATION OF 1, 3, 3, 3-TETRAFLUOROPROPENE AND 2, 3, 3, 3-TETRAFLUOROPROPENE

TECHNICAL FIELD

The present invention relates to a process for the preparation of hydrofluoroolefins, particularly to a process for the joint preparation of 1,3,3,3-tetrafluoropropene (HFO-1234ze) and 2,3,3,3-tetrafluoropropene (HFO-1234yf).

BACKGROUND ART

Hydrofluoroolefins (HFOs), as compared with chlorofluorocarbons (CFCs), Hydrochlorofluorocarbons (HCFCs) and hydrofluorohydrocarbons (HFCs), do not contain chlorine, do not pose a threat to the Earth's ozone layer, and present a low global warming potential, and they have now become the research focus in F-chemical industries. Tetrafluoropropene, such as 1,3,3,3-tetrafluoropropene (HFO-1234ze) and 2,3,3,3-tetrafluoropropene (HFO-1234yf), have an ozone depletion potential value of 0 and a global warming potential value less than 10, and they are widely used in the fields such as chemical industry, fire fighting, aerospace, aviation and the like, and can be used as refrigerants, foaming agents, fire extinguishing agents, heat transfer media, propellants, gaseous dielectrics, bactericidal agent carriers, polymer monomers and intermediates of medicine and pesticide.

US20110190554 discloses a method for the synthesis of HFO-1234yf from 1,1,2,3,3,3-hexafluoropropene (HFP) as a starting material via a four-step reaction including hydrogenation, dehydrofluorination, hydrogenation and dehydrofluorination. However, some drawbacks are present in the method including difficult accessibility, high cost of reaction materials, and the need of introducing at least the stoichiometric amount of hydrogen. Actually, a higher molar ratio is often used in order to effectively control the exothermicity of the reaction in the hydrogenation step. In addition, introduction of excessive hydrogen at a higher temperature will also increase relevant safety risks, and the conditions are harsh, which is not favorable to industrial production.

WO2012099776 discloses a method for preparing HFO-1234yf from 1,1,2,3-tetrachloropropene (TCP) via 2-chloro-3,3,3-trifluoropropene (HCFC-1233xf) and 2-chloro-1,1,1,2-tetrafluoropropane (HCFC-244bb) by integrated three steps. However, in this method, firstly, chromium-based catalysts such as $Cr_2O_3$ and $Cr_2O_3$ supported on alumina or fluorinated alumina are involved. In fact, chromium-based catalysts are often used in industrial production of HFCs. These chromium-containing compounds and catalysts will cause damage to digestive tract and kidney of human, especially high-valence chromium has strong carcinogenic effect, is not friendly and will cause serious harm to people and the environment. Secondly, the intermediates HCFC-1233xf and HCFC-244bb are involved. These two halogenated hydrocarbons have approximate boiling points and azeotrope-like properties, and both of them are also easy to form an azeotrope with HF. Hence, a problem of difficult separation occurs, and the mixtures of them cannot be separated effectively by standard process and conventional methods, especially when they form a binary azeotrope or azeotrope-like component. Additionally, it has been found that during the preparation of HFO-1234yf from HCFC-244bb by dehydrochlorination, the HCFO-1233xf and HF impurities contained therein can seriously affect the life and product selectivity of the dehydrochlorination catalyst, and easily lead to a decrease in HFO-1234yf selectivity and in activity of the catalyst and loss of the catalyst life.

At present, four methods have been mainly reported for preparation of HFO-1234ze including fluorine-chlorine exchange, dehydrohalogenation, telomerization and carbene reaction. With respect to fluorine-chlorine exchange, the method of synthesizing HFO-1234ze using 1-chloro-3,3,3-trifluoropropene (HCFC-1233zd) as material by one-step gas phase fluorination was reported in JP10007604, U.S. Pat. No. 6,472,573 and EP486333. However, the method has the disadvantage that the reaction material HCFC-1233zd is expensive, difficult to obtain, and inconvenient for transport. With respect to dehydrohalogenation, the method for synthesizing HFO-1234ze from 1,1,1,3,3-pentafluoropropane (HFC-245fa) as starting material was reported in U.S. Pat. No. 7,592,494, EP2014637, EP0974571, CN101265155, CN101466656 and JP10007605 respectively, but the reaction material HFC-245fa in the method is expensive. With respect to telomerization, US20050245773 and US20050245774 reported the preparation of HFO-1234ze using halogenated methane and halogenated ethylene as raw materials by telomerization followed by continuous fluorination. However, such synthesis method involves complicated route, the catalyst is expensive and prone to coking and deactivation, both the raw material conversion and the selectivity of target product are low. For preparation by carbene reaction, it has been reported in US20050245774 that HFO-1234ze can be obtained by reacting the difluorocarbene and vinylidene fluoride monomer in the same reactor at a high temperature above the cracking temperature of the difluorocarbene precursor. However, this synthesis method has no industrial application value with excessively high reaction temperature, low yield and harsh reaction conditions.

Although a number of methods have been currently disclosed for the preparation of HFO-1234ze and HFO-1234yf, they have shortcomings such as expensive and difficultly-accessible reaction materials, harsh reaction conditions, unfriendliness of the catalyst to environments, and difficult separation of reaction intermediates. Thus, there is a need for continuous improvement and more effective preparation methods.

SUMMARY OF THE INVENTION

The object of the present invention is to overcome the shortcomings in the background art and to provide a process for the joint preparation of 1,3,3,3-tetrafluoropropene and 2,3,3,3-tetrafluoropropene, in which the raw materials are inexpensive and easily accessible, the catalysts are environmentally friendly and the reaction conditions are mild.

To achieve the purpose of the present invention, the process for the joint preparation of 1,3,3,3-tetrafluoropropene and 2,3,3,3-tetrafluoropropene provided in the present invention is characterized in that, it comprises the following steps:

(a) starting materials comprising at least one compound having the structures of formula I, II or III, undergo fluorination reaction with hydrogen fluoride in the presence of a fluorination catalyst, producing a product stream containing 1,2,3-trichloro-3,3-difluoropropene, 1,2,3-trichloro-1,1,2-trifluoropropane, 1,2,3-trichloro-1,1,3-trifluoropropane, hydrogen chloride and unreacted hydrogen fluoride:

$$CF_{2-m}Cl_m\!=\!CCl\!-\!CHF_{2-n}Cl_n \qquad \text{(Formula I)}$$

$$CF_{3-p}Cl_pCHCl\!=\!CH_2Cl \qquad \text{(Formula II)}$$

$$CF_{3-x}Cl_xCF_{2-y}Cl_yCHF_{2-z}Cl_z \qquad \text{(Formula III)},$$

wherein in the general formulas of the compounds, m=0, 1, 2; n=1, 2; p=2, 3; x=1, 2, 3; y=1, 2; z=1, 2 and 4≤x+y+z≤6;

(b) 1,2,3-trichloro-3,3-difluoropropene, 1,2,3-trichloro-1,1,2-trifluoropropane and 1,2,3-trichloro-1,1,3-trifluoropropane undergo dechlorination in a reaction solvent under the action of zero-valent transition metal and organic nitrogen-containing ligand, producing 3-chloro-3,3-difluoropropyne, 3-chloro-2,3,3-trifluoropropene and 3-chloro-1,3,3-trifluoropropene; and (c) 3-chloro-3,3-difluoropropyne, 3-chloro-2,3,3-trifluoropropene, 3-chloro-1,3,3-trifluoropropene undergo gas phase fluorination reaction with hydrogen fluoride in the presence of a gas phase fluorination catalyst, producing a product stream containing 1,3,3,3-tetrafluoropropene, 2,3,3,3-tetrafluoropropene, hydrogen chloride and unreacted hydrogen fluoride, and separating to simultaneously yield 1,3,3,3-tetrafluoropropene and 2,3,3,3-tetrafluoropropene.

In the starting material in step (a), the compound of formula $CF_{2-m}Cl_m=CCl-CHF_{2-n}Cl_n$ is selected from the group consisting of $CCl_2=CCl-CHCl_2$, $CFCl=CCl-CHCl_2$, $CF_2=CCl-CHCl_2$, $CCl_2=CCl-CHFCl$, $CFCl=CCl-CHFCl$ and $CF_2=CCl-CHFCl$; the compound of formula $CF_{3-p}Cl_pCHCl=CH_2Cl$ is selected from the group consisting of $CCl_3CHCl=CH_2Cl$ and $CFCl_2CHCl=CH_2Cl$; the compound of formula $CF_{3-x}Cl_xCF_{2-y}Cl_yCHF_{2-z}Cl_z$ is selected from the group consisting of $CCl_3CCl_2CH_2Cl$, $CFCl_2CCl_2CH_2Cl$, $CF_2ClCCl_2CH_2Cl$, $CCl_3CFClCH_2Cl$, $CFCl_2CFClCH_2Cl$, $CCl_3CHClCHCl_2$, $CFCl_2CHClCHCl_2$, $CF_2ClCHClCHCl_2$, $CCl_3CHClCHFCl$ and $CFCl_2CHClCHFCl$.

In the starting material in step (a), the compound of formula $CF_{2-m}Cl_m=CCl-CHF_{2-n}Cl_n$ is $CCl_2=CCl-CHCl_2$; the compound of formula $CF_{3-p}Cl_pCHCl=CH_2Cl$ is $CCl_3CHCl=CH_2Cl$; the compound of formula $CF_{3-x}Cl_xCF_{2-y}Cl_yCHF_{2-z}Cl_z$ is $CCl_3CCl_2CH_2Cl$ or $CCl_3CHClCHCl_2$.

The starting material in step (a) comprises at least $CCl_2=CCl-CHCl_2$.

The fluorination catalyst described in step (a) is a Fe—Al—Mg—F compound catalyst in which the molar ratio of Fe, Al and Mg is (2-4):(1-2):(4-7). The preparation method of the catalyst comprises the following steps: dissolving soluble salts or alkoxides of the metals Fe, Al and Mg according to a certain ratio in corresponding alcohol solution under continuous stirring and ultrasonic conditions, adding a templating agent thereto, then adding precipitant to carry out the reaction, performing precipitation, filtration and drying, and then calcining by stages at 100° C. to 250° C. under the conditions of not less than three temperature gradients, and then activating in hydrogen fluoride atmosphere at 200° C. to 300° C.

The molar ratio of Fe, Al and Mg in the Fe—Al—Mg—F compound catalyst in step (a) is 2:1:7; the templating agent in the preparation method is polyethylene glycol; the fluorination reaction conditions are as follows: the reaction temperature is 100° C. to 240° C.; the molar ratio of hydrogen fluoride to starting material is 5-20:1, and the contact time is 3-20 seconds.

The fluorination reaction in step (a) comprises isomerization of 1,1,2,3,3-pentachloropropene to 1,2,3,3,3-pentachloropropene, and further comprises an addition reaction for converting 1,2,3-trichloro-3,3-difluoropropene to 1,2,3-trichloro-1,1,2-trifluoropropane and 1,2,3-trichloro-1,1,3-trifluoropropane.

The product stream in step (a) is introduced into a first rectification column for separation of hydrogen chloride. The component from the top of the column is hydrogen chloride which then enters an acid production system to give hydrochloric acid. The components from the bottom of the column are 1,2,3-trichloro-3,3-difluoropropylene, 1,2,3-trichloro-1,1,2-trifluoropropane, 1,2,3-trichloro-1,1,3-trifluoropropane and hydrogen fluoride, which enter a phase separator for phase separation; the phase separation temperature is −20° C. to 5° C., and the materials at the bottom of the phase separator, 1,2,3-trichloro-3,3-difluoropropene, 1,2,3-trichloro-1,1,2-trifluoropropane and 1,2,3-trichloro-1,1,3-trifluoropropane, are subjected to acid removal and drying before being dechlorinated as reaction materials of step (b).

The zero-valent transition metal in step (b) is Zn or Cu; the organic nitrogen-containing ligand is o-phenanthroline, 2,2-bipyridine, tris(2-pyridylmethyl)amine or tetramethyl ethylenediamine; and the reaction solvent is N,N-dimethylformamide or N-methylpyrrolidone.

The reaction conditions for the dechlorination reaction in step (b) are given as follows: the molar ratio of the reaction solvent to the total of 1,2,3-trichloro-3,3-difluoropropene, 1,2,3-trichloro-1,1,2-trifluoropropane and 1,2,3-trichloro-1,1,3-trifluoropropane is (5-20):1; the molar ratio of the zero-valent transition metal to the total of 1,2,3-trichloro-3,3-difluoropropene, 1,2,3-trichloro-1,1,2-trifluoropropane and 1,2,3-trichloro-1,1,3-trifluoropropane is (1-3):1; and the reaction temperature is 60° C. to 120° C.

The gas phase fluorination catalyst in step (c) is an Al—Co—Zn—F catalyst in which the molar ratio of Al, Co and Zn is (6-8):(1-2):(1-2); the reaction conditions for the gas phase fluorination reaction are given as follows: the reaction temperature is 150° C. to 240° C., the molar ratio of hydrogen fluoride to the total of 3-chloro-3,3-difluoropropyne, 3-chloro-2,3,3-trifluoropropylene and 3-chloro-1,3,3-trifluoropropene is (5-20):1, and the contact time is 0.1-20 seconds.

The gas phase fluorination reaction in step (c) further comprises isomerization among cis-1,3,3,3-tetrafluoropropene, trans-1,3,3,3-tetrafluoropropene and 2,3,3,3-tetrafluoropropene in the presence of Al—Co—Zn—F catalyst.

The product stream in step (c) enters a third rectification column. The components from the top of the column are 1,3,3,3-tetrafluoropropene, 2,3,3,3-tetrafluoropropene and hydrogen chloride, which are subjected to water washing, alkali washing and drying and then enters the refining process to give the target products 1,3,3,3-tetrafluoropropene and 2,3,3,3-tetrafluoropropene. The components from the bottom of the column are 3-chloro-2,3,3-trifluoropropylene, 3-chloro-1,3,3-trifluoropropene and HF, which are circulated to step (c) to continue the fluorination reaction.

The present invention as compared with the prior art has the following advantages: a method for effective joint preparation of 1,3,3,3-tetrafluoropropene and 2,3,3,3-tetrafluoropropene is provided; at the same time, the reaction materials are inexpensive and easily accessible, wherein $CCl_3CCl_2CH_2Cl$, $CCl_3CHCl=CH_2Cl$ and $CCl_2=CCl-CHCl_2$ are all commercially available, or obtainable by simple addition or elimination reaction or by the reaction of commercial halogenated methane with halogenated ethylene; the catalysts do not involve antimony-containing or chromium-containing compounds, being friendly to human and the environment; the reaction conditions are mild and the operation is simple, wherein the temperature of reaction, even the temperature of gas phase reaction, does not exceed 240° C.

BEST MODE OF THE INVENTION

The invention produces 1,3,3,3-tetrafluoropropene (HFO-1234ze) and 2,3,3,3-tetrafluoropropene (HFO-1234yf) using a starting material of the compound at least comprising $CCl_2=CCl-CHCl_2$ by three-steps reaction, i.e. fluorination, dechlorination and gas phase fluorination, the reaction process is as follows:

The process for the joint preparation of 1,3,3,3-tetrafluoropropene and 2,3,3,3-tetrafluoropropene according to the present invention comprises the following steps:

(a) a starting material comprising at least one compound having the structures of formula I, II or III undergoes fluorination reaction with hydrogen fluoride in the presence of a fluorination catalyst, producing a product stream containing 1,2,3-trichloro-3,3-difluoropropene (HCFO-1222xd), 1,2,3-trichloro-1,1,2-trifluoropropane (HCFC-233bc), 1,2,3-trichloro-1,1,3-trifluoropropane (HCFC-233db), hydrogen chloride (HCl) and unreacted hydrogen fluoride:

$CF_{2-m}Cl_m=CCl-CHF_{2-n}Cl_n$ (Formula I)

$CF_{3-p}Cl_pCHCl=CH_2Cl$ (Formula II)

$CF_{3-x}Cl_xCF_{2-y}Cl_yCHF_{2-z}Cl_z$ (Formula III), wherein in the general formulas of the compounds, m=0, 1, 2; n=1, 2; p=2, 3; x=1, 2, 3; y=1, 2; z=1, 2 and $4 \le x+y+z \le 6$;

(b) HCFO-1222xd, HCFC-233bc and HCFC-233db undergo dechlorination reaction in a reaction solvent under the action of zero-valent transition metal and organic nitrogen-containing ligand, producing 3-chloro-3,3-difluoropropyne, 3-chloro-2,3,3-trifluoropropene (HCFO-1233yf), 3-chloro-1,3,3-trifluoropropene (HCFO-1233ze); (c) 3-chloro-3,3-difluoropropyne, 3-chloro-2,3,3-trifluoropropene, 3-chloro-1,3,3-trifluoropropene undergo gas phase fluorination reaction with hydrogen fluoride in the presence of a gas phase fluorination catalyst, producing a product stream containing HFO-1234ze, HFO-1234yf, HCFO-1233yf, HCFO-1233ze, HCl and unreacted hydrogen fluoride.

In the starting material in step (a), the compound of the formula I $CF_{2-m}Cl_m=CCl-CHF_{2-n}Cl_n$ is selected from the group consisting of $CCl_2=CCl-CHCl_2$, $CFCl=CCl-CHCl_2$, $CF_2=CCl-CHCl_2$, $CCl_2=CCl-CHFCl$, $CFCl=CCl-CHFCl$ and $CF_2=CCl-CHFCl$, preferably $CCl_2=CCl-CHCl_2$; the compound of the formula II $CF_{3-p}Cl_pCHCl=CH_2Cl$ is selected from the group consisting of $CCl_3CHCl=CH_2Cl$ and $CFCl_2CHCl=CH_2Cl$, preferably $CCl_3CHCl=CH_2Cl$; the compound of the formula III $CF_{3-x}Cl_xCF_{2-y}Cl_yCHF_{2-z}Cl_z$ is selected from the group consisting of $CCl_3CCl_2CH_2Cl$, $CFCl_2CCl_2CH_2Cl$, $CF_2ClCCl_2CH_2Cl$, $CCl_3CFClCH_2Cl$, $CFCl_2CFClCH_2Cl$, $CCl_3CHClCHCl_2$, $CFCl_2CHClCHCl_2$, $CF_2ClCHClCHCl_2$, $CCl_3CHClCHFCl$ and $CFCl_2CHClCHFCl$, preferably $CCl_3CCl_2CH_2Cl$ and $CCl_3CHClCHCl_2$. These preferred reaction materials are all commercially available, or obtainable by simple addition or elimination reaction or by the reaction of commercial halogenated methane with halogenated ethylene. In the present invention, the starting material of the step (a) is one or two or more compounds containing at least $CCl_2=CCl-CHCl_2$. In the step (a) of the present invention, the starting material may be supplied to the reactor as it is, or may be supplied to the reactor after being diluted with an inert gas such as nitrogen, helium or argon.

The fluorination catalyst in step (a) of the present invention is a Fe—Al—Mg—F compound catalyst in which the molar ratio of Fe, Al and Mg is (2-4):(1-2):(4-7), preferably 2:1:7. The preparation method of the catalyst comprises the following steps: dissolving soluble salts or alkoxides of the metals Fe, Al and Mg according to a certain ratio in corresponding alcohol solution under continuous stirring and ultrasonic conditions, adding a templating agent thereto, then adding a specific amount of precipitant to carry out the reaction, performing precipitation, filtration and drying, and then calcining by stages at 100° C. to 250° C. under the conditions of not less than three temperature gradients, and then activating in hydrogen fluoride atmosphere at 200° C. to 300° C. During the preparation process, the ultrasonic conditions have an important effect on the preparation of the catalyst. Wherein, the templating agent is polyethylene glycol, such as polyethylene glycol-4000, polyethylene glycol-2000, and polyethylene glycol-600. Suitable catalysts also include, but are not limited to, one or a mixture of two or more of oxides, hydroxides, halides, oxyhalides and inorganic salts of chromium, aluminum, cobalt, manganese, nickel and iron. Certainly, it may also be fluorinated activated carbon, SbCl$_5$ or TiCl$_4$ supported on activated carbon, magnesium fluoride, chromium oxide added with a variety of metals (such as Zn, Co, Ni, Ge, In, etc.) and others. The fluorination reaction of step (a) of the present invention may also be a liquid phase reaction conducted with HF in the presence of a liquid phase fluorination catalyst, wherein the liquid phase fluorination catalyst is a Lewis acid, a transition metal halide, a transition metal oxide, or a combination thereof, for example, hexavalent molybdenum halide, pentavalent arsenic halide, tetravalent titanium halide, tetravalent tin halide, trivalent iron halide, trivalent antimony halide, trivalent chromium fluoride, fluoride of chromic oxide, halosulfonic acid, or combinations thereof.

The temperature of the fluorination reaction of step (a) according to the present invention is an important factor influencing the gas phase catalytic fluorination reaction, and the choice of a suitable temperature enables the production of the target products HCFO-1222xd, HCFC-233bc and HCFC-233db with high selectivity. The reaction temperature is in the range of 100° C. to 240° C., preferably 150° C. to 200° C. When the temperature is too high, it leads to the generation of HCFO-1223xd, 2,3-dichloro-1,1,1,2-tetrafluoropropane (HCFC-234bb) and 2,3-dichloro-1,1,1,3 tetrafluoropropane (HCFC-234da), and meanwhile it may also result in the coking and inactivation of the catalyst; when the temperature is too low, the conversion rate of the reaction decreases, HCFO-1222xd is produced mainly with only a small amount of HCFC-233bc and HCFC-233db generated.

The fluorination reaction in step (a) of the present invention also comprises isomerization reaction for converting HCO-1220xa to 1,2,3,3,3-pentachloropropene under the action of a Fe—Al—Mg—F compound catalyst, and further comprises addition reaction for converting HCFO-1222xd to HCFC-233bc and HCFC-233db.

The reaction pressure of step (a) of the present invention has little effect on the fluorination reaction, and a convenient operating pressure can be selected depending on the material of the reaction apparatus, the degree of corrosion resistance and the degree of pressure resistance thereof. Preferably, the reactor is made of a material resistant to corrosion of hydrogen fluoride and the catalyst, such as Hastalloy, Inconel, Monel, and a container lined with fluoropolymer.

The product stream containing HCFO-1222xd, HCFC-233bc, HCFC-233db, HCl and unreacted HF from step (a) of the present invention is introduced into a first rectification column for HCl separation. The component from the top of the column is hydrogen chloride which then enters an acid production system to give hydrochloric acid. The components from the bottom of the column are HCFO-1222xd, HCFC-233bc, HCFC-233db and HF, which enter a phase separator for phase separation; the phase separation temperature is −20° C. to 5° C., and the materials at the bottom of the phase separator, HCFO-1222xd, HCFC-233bc, and HCFC-233db, are subjected to acid removal and drying before being dechlorinated as reaction materials of step (b). If the product stream from step (a) contains unreacted starting material, the product stream is passed to the first rectification column to remove hydrogen chloride, the materials from the bottom of the column are either circulated back to the reactor through a heat exchanger or enter a second rectification column, depending on the content of the unreacted starting material therein. For the second rectification column, the components from the top of the column are HCFO-1222xd, HCFC-233bc, HCFC-233db and HF, which then enter the phase separator for phase separation, and the components from the bottom of the column are unreacted reaction materials and hydrogen fluoride, which are then returned back to the reactor through a heat exchanger. Preferably, when the content of unreacted starting material in the organic components of the product is higher than 6%, the latter is adopted.

The zero-valent transition metal in step (b) of the present invention is Zn or Cu, and the zero-valent metal may also be Ag, Ni, Fe or a bimetallic system of Ag and Fe, or a composition of Cu and Fe, or a composition of Pd and Fe. The organic nitrogen-containing ligand in step (b) is o-phenanthroline, 2,2-bipyridine, tris (2-pyridylmethyl) amine or tetramethylethylenediamine; the reaction solvent is N,N-dimethylformamide or N-methylpyrrolidone; suitable reaction solvents also include polar aprotic solvents such as DMSO, NMP, polyethylene glycol 400, and partial polar protic solvents. The amount of the reaction solvent is preferably ten folds of the total molar amount of HCFO-1222xd, HCFC-233bc and HCFC-233db, and the reaction temperature is 60° C. to 120° C., preferably 90° C.

The gas phase fluorination catalyst in step (c) of the present invention is an Al—Co—Zn—F catalyst, and the molar ratio of Al, Co and Zn is an important factor influencing the fluorination reaction, and the molar ratio is (6-8):(1-2):(1-2), preferably 7:2:1. Methods suitable for the preparation of the catalyst include impregnation method, coprecipitation method, blending method or gel-sol method.

Control on the reaction temperature of step (c) of the present invention is one of the key factors in the gas phase catalytic fluorination reaction, and the reaction temperature is in the range of 150° C. to 240° C., preferably 180° C. to 200° C. When the temperature is too high, polymerization byproducts increase, severe carbon deposition of the catalyst occurs, resulting in inactivation of the catalyst and loss of life. When the temperature is too low, the conversion rate of the reaction will be reduced unfavorably, the selectivity ratio of the trans-HFO-1234ze, which exhibits better effect as a refrigerant, to the cis-HFO-1234ze will decrease. In particular, when the reaction is carried out at a temperature higher than 260° C., carbides will be generated and adhered to or deposited on the reaction tube wall or filler, and the inside of the reactor is gradually blocked. In view of this situation, the reaction material can be diluted with a specific amount of inert gas such as nitrogen, helium or argon to relieve or eliminate the above situation. In addition, the reaction can be suspended, and oxygen or air is introduced into the reactor to remove the carbide residue in the reaction tube.

The gas phase fluorination reaction in step (c) of the present invention also includes isomerization reaction for the conversion among cis-HFO-1234ze, trans-HFO-1234ze and 2 HFO-1234yf under the action of Al—Co—Zn—F catalyst.

The product stream containing HFO-1234ze, HFO-1234yf, HCFO-1233yf, HCFO-1233ze, HCl and unreacted HF in the step (c) of the present invention enters a third rectification column. The components from the top of the column are HFO-1234ze, HFO-1234yf and HCl, which subsequently undergoes water washing, alkali washing and drying and then enters the refining process to give the target products HFO-1234ze and HFO-1234yf. The components from the bottom of the column are HCFO-1233yf, HCFO-1233ze and HF, which are circulated to step (c) to conduct fluorination reaction continuously.

None of the catalysts in steps (a), (b), and (c) of the present invention involve antimony-containing or chromium-containing compounds, and the catalysts are friendly to human health and environment.

The present invention will now be described in further detail with reference to examples.

Analytical instruments: Haixin Gas Chromatograph GC-930, Agilent, 30 m DB-5 (50 m×0.32 mm) capillary chromatographic Column; ITQ 700 (ion trap): Thermofisher scientific, Agilent GASPRO (60 m×0.25 mm) capillary chromatographic column.

Chromatographic conditions: an initial column temperature of 40° C., keeping for 5 min, heating at a rate of 10° C./min to 180° C., and keeping for 3 min; a vaporizing chamber temperature of 220° C., and a split ratio of 50.

The conditions for ion trap mass spectrometry: a filament emission current of 70 A; a mass scanning range of 10-350 amu; full scan mode, a scan speed of 10 micro-scan/sec; a multiplier voltage of 1556V; a transmission line temperature of 220° C., helium as carrier gas.

Example 1

Figure 1:
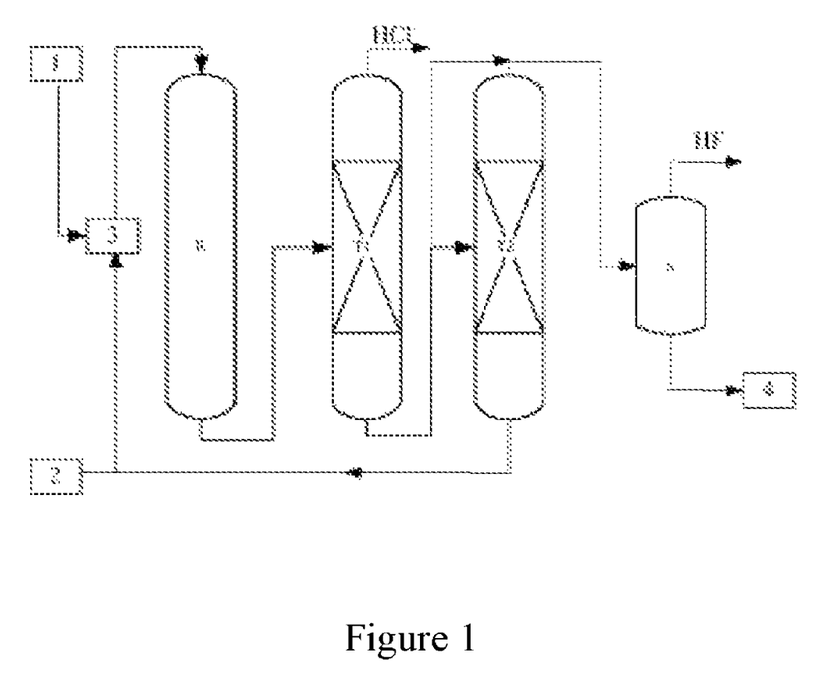
FIG. 1 is a schematic flow diagram of step (a), wherein R is a reactor, T1 is a first rectification column, T2 is a second rectification column, S is a phase separator, 1 is the starting material, 2 is hydrogen fluoride, 3 is a static mixer and/or heat exchanger, and 4 is a dechlorination reaction system.

Further explanation of the schematic flow diagram of step (a):

First, The raw material 1 was-fully mixed with hydrogen fluoride 2 in a static mixer and/or a heat exchanger 3, and then entered the reactor R to carry out reaction. The products entered the first rectification column T1 for separation of HCl. The component from the top of the column was hydrogen chloride which then entered an acid production system to give hydrochloric acid. The components from the bottom of the column were HCFO-1222xd, HCFC-233bc, HCFC-233db and HF, which entered a phase separator S for phase separation; the phase separation temperature was −30° C. to 0° C., and the materials at the bottom of the phase separator, HCFO-1222xd, HCFC-233bc, and HCFC-233db, were subjected to acid removal and drying before being dechlorinated as reaction materials of step (b). If the reaction product of step (a) contained unreacted starting material, and when the content of the unreacted starting material was higher than 6% in the organic components of the product, the reaction product stream entered the first rectification column T1 to remove HCl, the materials from the bottom of the column entered the second rectification column T2. The components from the top of the column were HCFO-1222xd, HCFC-233bc, HCFC-233db and HF, which entered the phase separator S for phase separation. The components from the bottom of the column were unreacted starting material and HF, which were circulated through a static mixer and/or heat exchanger 3 to the reactor R.

Preparation of the catalyst: certain amounts of $Fe(NO_3)_2 \cdot 9H_2O$, $Al(NO_3)_2 \cdot 9H_2O$ and $Mg(NO_3)_2 \cdot 6H_2O$ were accurately weighed according to a certain ratio, dissolved in anhydrous ethanol, and added with a certain amount of polyethylene glycol-4000. The resulting mixed ethanol solution was added dropwise to 40% HF solution at 40° C. under continuous stirring and ultrasonic conditions for about 3 hours. Then, precipitation was carried out, and the precipitate was filtered, washed, dried at 70° C. for 2 h, and then calcined in a muffle furnace as follows: calcining at 100° C. for 1 h, heating at a rate of 5° C./min to 200° C., calcining for 2 h, then heating at a rate of 10° C./min to 250° C., and calcining for 4 h.

In a fixed-bed tubular reactor having an inner diameter of 38 mm, 50 ml of the above Fe—Al—Mg—F compound catalyst was charged in which the molar ratio of Fe, Al and Mg was 2:1:7, and the catalyst was dried, and then activated at 200° C. to 300° C. in a hydrogen fluoride atmosphere. Subsequently HF was introduced at 150° C., and then 1,1,2,3,3-pentachloropropene and 1,1,1,2,2,3-hexachloropropane (the molar percentages of both are 70% and 30%, respectively) were introduced. Reaction was carried out at atmospheric pressure (normal pressure) with the molar ratio of HF to the starting materials being 15:1 and contact time of 10 s. The reaction products were washed with water and alkali to remove HCl and HF. Analysis was carried out by gas chromatography and mass spectrometry, the products mainly comprise HCFO-1222xd, HCFC-233bc and HCFC-233db, and at the same time comprise a small amount of HCFO-1223xd, HCFC-234bb and HCFC-234da. The reaction results were shown in Table 1.

Figure 2:
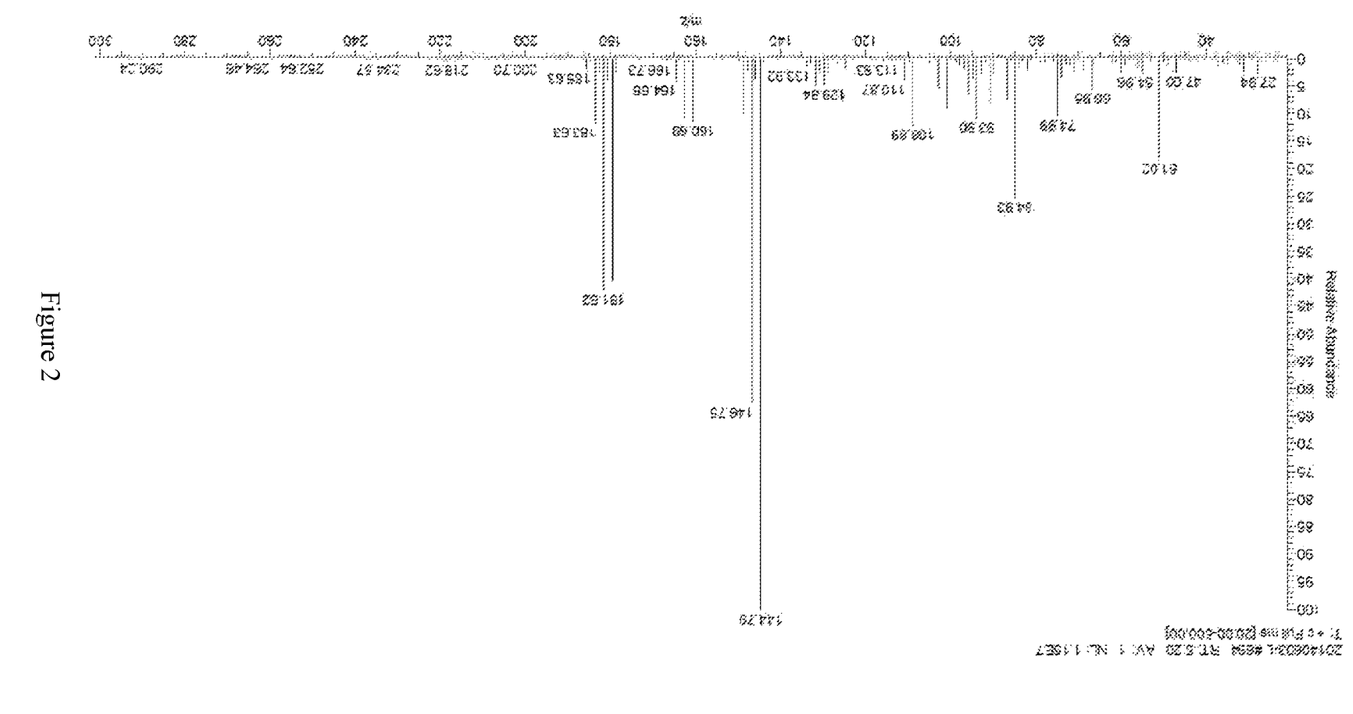
FIG. 2 is the GC-MS spectrum of the product HCFO-1222xd.

The above liquid reaction product was rectified, and the product with a boiling point of 108° C. to 110° C. was collected and characterized by GC-MS as HCFO-1222xd, as shown in FIG. 2.

The results of the mass spectrum shown in FIG. 2 and assignment of its peaks are as follows: presence of molecular ion peaks, m/z180:m/z182:m/z184:m/z186=27:27:9:1 ($M^+$), which is the isotope peak ratio of the fragment containing three chlorine atoms; m/z161:m/z163:m/z165:m/z167=27:27:9:1 [$(M-F)^+$], which is the isotope peak ratio of the fragment containing three chlorine atoms; m/z145:m/z147:m/z149=9:6:1 [$(M-Cl)^+$], which is the isotope peak ratio of the fragment containing two chlorine atoms; m/z109:m/z111=3:1 [$(M-Cl—HCl)^+$], which is the isotope peak ratio of the fragment containing one chlorine atom; m/z85:m/z87=3:1 ($^+CF_2Cl$), m/z75 ($C_3HF_2^+$), m/z51 ($CHF_2^+$); the loss is reasonable, and the compound is HCFO-1222xd.

Figure 3:
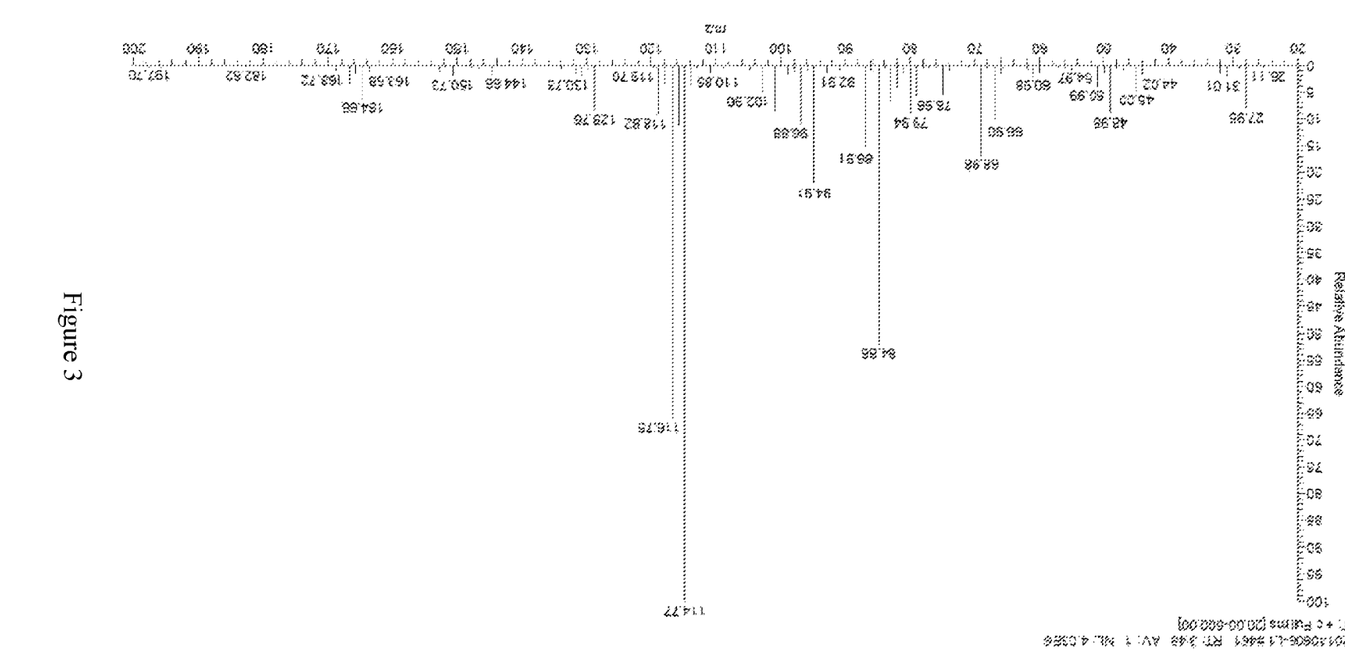
FIG. 3 is the GC-MS spectrum of the product HCFC-233bc.

The above liquid reaction product was rectified, and the product with a boiling point of 96° C. to 97° C. was collected and characterized by GC-MS as HCFC-233bc, as shown in FIG. 3.

The results of the mass spectrum shown in FIG. 3 and assignment of its peaks are as follows: M/z165:m/z167:m/z169=9:6:1 [$(M-Cl)^+$], which is the isotope peak ratio of the fragment containing two chlorine atoms; m/z129:m/z131=3:1[$(M-Cl—HCl)^+$], which is the isotope peak ratio of the fragment containing one chlorine atom; m/z115:m/z117:m/z119=9:6:1($CH_2FCl_2^+$), which is the isotope peak ratio of the fragment containing two chlorine atoms, the fragment and the fragment of m/z85: m/z87=3:1($^+CF_2Cl$) are complementary ions, m/z75($C_3HF_2^+$), m/z67:m/z69=3:1($^+CHFCl$), m/z49:m/z51=3:1($^+CH_2Cl$); the loss is reasonable, and the compound is HCFC-233bc.

Examples 2-5

In Examples 2-5, the reaction was carried out in the same manner as in Example 1 except that the reaction temperature in Example 1 was 150° C. while the reaction temperatures in Examples 2-5 were 100° C., 180° C., 200° C., and 240° C. respectively. The results were shown in Table 1.

TABLE 1

| Example | reaction temperature (° C.) | Conversion rates (%) | selectivity (%) | | |
|---|---|---|---|---|---|
| | | | HCFO-1222xd | HCFC-233bc | HCFC-233db |
| 1 | 150 | 100 | 75.6 | 12.3 | 10.4 |
| 2 | 100 | 76.9 | 80.4 | 12.8 | 6.5 |
| 3 | 180 | 100 | 64.7 | 18.1 | 15.2 |
| 4 | 200 | 100 | 51.3 | 24.9 | 20.5 |
| 5 | 240 | 100 | 30.4 | 33.7 | 30.6 |

Examples 6-8

In Examples 6-8, the reaction was carried out in the same manner as in Example 1 except that the molar ratio of Fe, Al and Mg in the catalyst of Example 1 was 2:1:7 while the molar ratios in the catalysts of Examples 6-8 were 2:2:6, 3:1:6 and 4:2:4 respectively. The reaction results were shown in Table 2.

TABLE 2

| Example | Fe, Al, Mg molar ratio | Conversion rates (%) | selectivity (%) | | |
|---|---|---|---|---|---|
| | | | HCFO-1222xd | HCFC-233bc | HCFC-233db |
| 6 | 2:2:6 | 100 | 82.8 | 10.6 | 5.1 |
| 7 | 3:1:6 | 100 | 59.2 | 20.5 | 18.3 |
| 8 | 4:2:4 | 100 | 65.6 | 16.3 | 14.0 |

Examples 9-11

In Examples 9-11, the reaction was carried out in the same manner as in Example 1 except that the molar ratio of HF to the starting reaction material in Example 1 was 15:1 while the molar ratio of both in Examples 9-11 were 5:1, 10:1 and 20:1 respectively. The results were shown in Table 3.

TABLE 3

| Example | molar ratio of the reaction materials | Conversion rates (%) | selectivity (%) | | |
|---|---|---|---|---|---|
| | | | HCFO-1222xd | HCFC-233bc | HCFC-233db |
| 9 | 5:1 | 95.9 | 81.6 | 9.7 | 6.2 |
| 10 | 10:1 | 97.2 | 77.1 | 11.8 | 8.6 |
| 11 | 20:1 | 100 | 74.8 | 12.9 | 10.5 |

Examples 12-14

In Examples 12-14, the reaction was carried out in the same manner as in Example 1 except that the contact time in Example 1 was 10 s while the contact times in examples 12-14 were 3 s, 5 s and 20 s respectively. The results were shown in Table 4.

TABLE 4

| Example | contact time (s) | Conversion rates (%) | selectivity (%) | | |
|---|---|---|---|---|---|
| | | | HCFO-1222xd | HCFC-233bc | HCFC-233db |
| 12 | 3 | 93.6 | 87.6 | 8.7 | 3.2 |
| 13 | 5 | 95.3 | 83.6 | 9.1 | 5.4 |
| 14 | 20 | 100 | 62.4 | 17.8 | 15.1 |

Example 15

The reaction was carried out in the same manner as in Example 1 except that the starting material in Example 1 was a composition of 1,1,2,3,3-pentachloropropene and 1,1,1,2,2,3-hexachloropropane while the starting material for the reaction of Example 15 was a composition of 1,1,2,3,3-pentachloropropene, 1,2,3,3,3-pentachloropropene and 1,1,1,2,3,3-hexachloropropane (mole percentages are 50%, 20% and 30%, respectively). The results showed that the selectivities of HCFO-1222xd, HCFC-233bc and HCFC-233db were 55.0%, 12.2% and 30.7%, respectively.

Example 16

The reaction was carried out in the same manner as in Example 1 except that the starting material in Example 1 was a composition of 1,1,2,3,3-pentachloropropene and 1,1,1,2,2,3-hexachloropropane while the starting material for Example 16 was 1,1,2,3,3-pentachloropropene. The result showed that the selectivities of HCFO-1222xd, HCFC-233bc and HCFC-233db were 90.5%, 5.3% and 2.8%, respectively.

Example 17

To a 100 mL Monel autoclave equipped with a magnetic stirrer, a packed column and a condenser assembly, 20 g of HCFO-1222xd, HCFC-233bc, HCFC-233db (the mass percentages of the three were 52.4%, 25.3% and 21.0%, respectively), zinc powder (9.4 g, 0.14 mol), 18.9 g of o-phenanthroline and 65 mL of DMF were added, gradually heated to 90° C. and maintained at this temperature for 6 h. After cooling, the product was discharged from the top of the condenser to a water absorber connected with a −78° C. cold trap. The reaction results were analyzed by gas chromatography. The results were shown in Table 5, wherein the conversion rate of the dechlorination reaction was the sum of the conversion rates of HCFO-1222xd, HCFC-233bc and HCFC-233db.

Examples 18-19

In Examples 18 and 19, the reaction was carried out in the same manner as in Example 17 except that the reaction temperature in Example 17 was 90° C. while the reaction temperatures were 60° C. and 120° C. in examples 18 and 19, respectively. The results were shown in Table 5.

TABLE 5

| Example | reaction temperature (° C.) | dechlorination conversion rate (%) | product distribution (%) | | |
|---|---|---|---|---|---|
| | | | 3-chloro-3,3-difluoropropyne | 1233yf | 1233ze |
| 17 | 90 | 84.8 | 46.4 | 26.1 | 21.8 |
| 18 | 60 | 73.5 | 31.6 | 35.3 | 30.2 |
| 19 | 120 | 97.3 | 54.6 | 18.7 | 17.0 |

Examples 20-22

In Examples 20-22, the reaction was carried out in the same manner as in Example 17 except that the amount of zinc powder used in Example 17 was 9.4 g while the amount of zinc powder used in Examples 20-22 were 7.8 g, 15.6 g, 23.4 g, respectively, and o-phenanthroline ligands were increased proportionally. The reaction results were shown in Table 6.

TABLE 6

| Example | zinc powder (g) | dechlorination conversion rate (%) | product distribution (%) | | |
|---|---|---|---|---|---|
| | | | 3-chloro-3,3-difluoropropyne | 1233yf | 1233ze |
| 20 | 7.8 | 78.6 | 29.3 | 36.0 | 31.1 |
| 21 | 15.6 | 95.4 | 45.5 | 25.4 | 21.0 |
| 22 | 23.4 | 97.7 | 45.3 | 25.1 | 20.6 |

Examples 23-25

In Examples 23-25, the reaction was carried out in the same manner as in Example 17 except that the molar ratio of the reaction solvent DMF to the total of HCFO-1222xd, HCFC-233bc and HCFC-233db in Example 17 was 10:1, while the molar ratio in Examples 23-25 were 5:1, 15:1 and 20:1, respectively.

TABLE 7

| Example | amount of the reaction solvent | dechlorination conversion rate (%) | product distribution (%) | | |
|---|---|---|---|---|---|
| | | | 3-chloro-3,3-difluoropropyne | 1233yf | 1233ze |
| 23 | 5:1 | 78.4 | 32.3 | 35.0 | 30.9 |
| 24 | 15:1 | 85.5 | 41.2 | 28.9 | 26.6 |
| 25 | 20:1 | 86.8 | 42.5 | 29.8 | 25.3 |

Examples 26-28

In Examples 26-28, the reaction was carried out in the same manner as in Example 17 except that the reducing agent in Example 17 was zinc powder while the zero valent metal in Examples 26-28 was copper powder, bimetal Ag/Fe, and bimetal Pd/Ni, respectively. The reaction results were shown in Table 8.

TABLE 8

| Example | zero-valent metal | dechlorination conversion rate (%) | product distribution (%) | | |
|---|---|---|---|---|---|
| | | | 3-chloro-3,3-difluoropropyne | 1233yf | 1233ze |
| 26 | Cu | 86.4 | 47.1 | 26.9 | 21.7 |
| 27 | Ag/Fe | 88.3 | 39.5 | 25.4 | 20.2 |
| 28 | Pd/Ni | 100 | 55.2 | 19.7 | 17.8 |

Example 29

In Example 29, the reaction was carried out in the same manner as in Example 17 except that the reaction material in Example 17 was a mixture of HCFO-1222xd, HCFC-233bc and HCFC-233db (the mass percentages thereof were 52.4%, 25.3% and 21.0%, respectively) while the reaction material in Example 29 was HCFO-1222xd. The reaction results showed that the conversion rate of the reaction was 90.5% and the selectivity of 3-chloro-3,3-difluoropropyne was 98.9%.

Example 30

Preparation of the catalyst: $Al(NO_3)_3 \cdot 9H_2O$, $Co(NO_3)_2 \cdot 6H_2O$ and $Zn(NO_3)_2 \cdot 6H_2O$ were accurately weighed according to a certain ratio, then 10% (by mass) ammonia was added dropwise to a mixed aqueous solution of the above three substances, and the pH was adjusted and controlled at about 7-9 for about 6 h. The product was washed, separated centrifugally, dried at 120° C., and then calcined as follows: calcining at 200° C. for 1 h, heating at a rate of 5° C./min to 300° C., calcining for 2 h, then heating at a rate of 5° C./min to 450° C. and calcining for 4 h.

In a fixed-bed tubular reactor having an inner diameter of 38 mm, 50 ml of the above Al—Co—Zn—F catalyst was charged in which the molar ratio of Al, Co and Zn was 7:2:1, and the catalyst was dried and activated. After activation was finished, HF was introduced at 180° C., and then 3-chloro-3,3-difluoropropyne, HCFO-1233yf and HCFO-1233ze (the mass percentages thereof were 49.3%, 34.1% and 15.5%, respectively) were introduced. Reaction was carried out at atmospheric pressure (normal pressure) with the molar ratio of HF to the total of 3-chloro-3,3-difluoropropyne, HCFO-1233yf and HCFO-1233ze being 15:1 and contact time of 15 s. The reaction products were washed with water and alkali to remove HCl and HF. Analysis was carried out by gas chromatography and mass spectrometry. The results are shown in Table 9, wherein the conversion rate of fluorination reaction was the sum of conversion rates of 3-chloro-3,3-difluoropropyne, HCFO-1233yf and HCFO-1233ze.

Examples 31-33

In Examples 31-33, 1,3,3,3-tetrafluoropropene (trans-HFO-1234ze and cis-HFO-1234ze, abbreviated as trans-1234ze and cis-1234ze, respectively) and 2,3,3,3-tetrafluoropropene (HFO-1234yf, abbreviated as 1234yf) were jointly prepared in the same manner as in Example 30, except that the reaction temperature in Example 30 was 180° C. while the reaction temperatures in Examples 31-33 were 150° C., 200° C. and 240° C., respectively. The reaction results were shown in Table 9.

TABLE 9

| Example | reaction temperature (° C.) | conversion rate (%) | product distribution (%) | | |
|---|---|---|---|---|---|
| | | | 1234yf | trans-1234ze | cis-1234ze |
| 30 | 180 | 95.8 | 85.1 | 9.9 | 1.3 |
| 31 | 150 | 86.6 | 87.2 | 9.9 | 1.0 |
| 32 | 200 | 100 | 81.5 | 11.9 | 1.7 |
| 33 | 240 | 100 | 76.9 | 12.8 | 2.6 |

Examples 34-36

In Examples 34-36, 1,3,3,3-tetrafluoropropene and 2,3,3,3-tetrafluoropropene were jointly produced in the same manner as in Example 30, except that the molar ratio of Al, Co and Zn in the catalyst of Example 30 was 7:2:1, while the molar ratio of Al, Co and Zn in the catalysts of Examples 34-36 were 6:2:2, 7:1:2 and 8:1:1, respectively. The results were shown in Table 10.

TABLE 10

| Example | Al, Co, Zn molar ratio | conversion rate (%) | product distribution (%) | | |
|---|---|---|---|---|---|
| | | | 1234yf | trans-1234ze | cis-1234ze |
| 34 | 6:2:2 | 91.6 | 86.9 | 10.4 | 1.0 |
| 35 | 7:1:2 | 94.8 | 83.5 | 12.2 | 1.7 |
| 36 | 8:1:1 | 98.4 | 82.3 | 12.3 | 2.3 |

Examples 37-38

In Examples 37 and 38, 1,3,3,3-tetrafluoropropene and 2,3,3,3-tetrafluoropropene were jointly produced in the same manner as in Example 30, except that the molar ratio of hydrogen fluoride to the total of 3-chloro-3,3-difluoropropyne, HCFO-1233yf and HCFO-1233ze in Example 30 was 15:1 while the molar ratios in Examples 37 and 38 were 10:1 and 20:1, respectively. The reaction results were shown in Table 11.

TABLE 11

| Example | molar ratio | conversion rate (%) | product distribution (%) | | |
|---|---|---|---|---|---|
| | | | 1234yf | trans-1234ze | cis-1234ze |
| 37 | 10:1 | 96.1 | 86.4 | 9.7 | 1.2 |
| 38 | 20:1 | 94.7 | 83.3 | 11.1 | 1.4 |

Examples 39-41

In Examples 39-41, 1,3,3,3-tetrafluoropropene and 2,3,3,3-tetrafluoropropene were jointly produced in the same manner as in Example 30, except that the contact time in Example 30 was 15 s while the contact time in Examples 39-41 were 5 s, 10 s, and 20 s, respectively. The results were shown in Table 12.

TABLE 12

| Example | contact time (s) | conversion rate (%) | product distribution (%) | | |
|---|---|---|---|---|---|
| | | | 1234yf | trans-1234ze | cis-1234ze |
| 39 | 5 | 85.5 | 80.1 | 16.2 | 2.2 |
| 40 | 10 | 93.4 | 83.2 | 12.0 | 1.7 |
| 41 | 20 | 100 | 87.3 | 8.3 | 0.8 |

Example 42

The reaction was carried out in the same manner as in Example 30, except that the reaction material in Example 30 was a composition of 3-chloro-3,3-difluoropropyne, HCFO-1233yf and HCFO-1233ze (the mass percentages thereof were 49.3%, 34.1% and 15.5%, respectively) while the reaction material of Example 42 was 3-chloro-3,3-difluoropropyne. The results showed the selectivities of HFO-1234yf, trans-HFO-1234ze and cis-HFO-1234ze were 60.7%, 34.9% and 4.0%, respectively.

The foregoing is only a part of examples of the present invention, and is not intended to limit the present invention. Any simple alternations, equivalent variations and modifications to the above-described examples in accordance with the technical essence of the present invention fall within the scope of the technical solutions of the present invention.

What is claimed is:

1. A process for the joint preparation of 1,3,3,3-tetrafluoropropene and 2,3,3,3-tetrafluoropropene comprising the following steps:
   (a) starting materials comprising at least one compound having the structures of formula I, II or III, undergo fluorination reaction with hydrogen fluoride in the presence of a fluorination catalyst, producing a product stream containing 1,2,3-trichloro-3,3-difluoropropene, 1,2,3-trichloro-1,1,2-trifluoropropane, 1,2,3-trichloro-1,1,3-trifluoropropane, hydrogen chloride and unreacted hydrogen fluoride;

$$CF_{2-m}Cl_m=CCl-CHF_{2-n}Cl_n \quad \text{(Formula I)}$$

$$CF_{3-p}Cl_pCHCl=CH_2Cl \quad \text{(Formula II)}$$

$$CF_{3-x}Cl_xCF_{2-y}Cl_yCHF_{2-z}Cl_z \quad \text{(Formula III),}$$

wherein in the general formulas of the compounds, m=0, 1, 2; n=1, 2; p=2, 3; x=1, 2, 3; y=1, 2; z=1, 2 and 4≤x+y+z≤6;
   (b) 1,2,3-trichloro-3,3-difluoropropene, 1,2,3-trichloro-1,1,2-trifluoropropane and 1,2,3-trichloro-1,1,3-trifluoropropane undergo dechlorination reaction in a reaction solvent under the action of zero-valent transition metal and organic nitrogen-containing ligand, producing 3-chloro-3,3-difluoropropyne, 3-chloro-2,3,3-trifluoropropene and 3-chloro-1,3,3-trifluoropropene; and
   (c) 3-chloro-3,3-difluoropropyne, 3-chloro-2,3,3-trifluoropropene and 3-chloro-1,3,3-trifluoropropene undergo gas phase fluorination with hydrogen fluoride in the presence of a gas phase fluorination catalyst, simultaneously yielding 1,3,3,3-tetrafluoropropene and 2,3,3,3-tetrafluoropropene.

2. The process for the joint preparation of 1,3,3,3-tetrafluoropropene and 2,3,3,3-tetrafluoropropene according to claim 1, characterized in that, in the starting material in step (a), the compound of formula $CF_{2-m}Cl_m=CCl-CHF_{2-n}Cl_n$ is selected from the group consisting of $CCl_2=CCl-CHCl_2$, $CFCl=CCl-CHCl_2$, $CF_2=CCl-CHCl_2$, $CCl_2=CCl-CHFCl$, $CFCl=CCl-CHFCl$ and $CF_2=CCl-CHFCl$; the compound of formula $CF_{3-p}Cl_pCHCl=CH_2Cl$ is selected from the group consisting of $CCl_3CHCl=CH_2Cl$ and $CFCl_2CHCl=CH_2Cl$; the compound of formula $CF_{3-x}Cl_xCF_{2-y}Cl_yCHF_{2-z}Cl_z$ is selected from the group consisting of $CCl_3CCl_2CH_2Cl$, $CFCl_2CCl_2CH_2Cl$, $CF_2ClCCl_2CH_2Cl$, $CCl_3CFClCH_2Cl$, $CFCl_2CFCH_2Cl$, $CCl_3CHClCHCl_2$, $CFCl_2CHClCHCl_2$, $CF_2ClCHClCHCl_2$, $CCl_3CHClCHFCl$ and $CFCl_2CHClCHFCl$.

3. The process for the joint preparation of 1,3,3,3-tetrafluoropropene and 2,3,3,3-tetrafluoropropene according to claim 2, characterized in that, in the starting material in step (a), the compound of formula $CF_{2-m}Cl_m=CCl-CHF_{2-n}Cl_n$ is $CCl_2=CCl-CHCl_2$; the compound of formula $CF_{3-p}Cl_pCHCl=CH_2Cl$ is $CCl_3CHCl=CH_2Cl$; the compound of formula $CF_{3-x}Cl_xCF_{2-y}Cl_yCHF_{2-z}Cl_z$ is $CCl_3CCl_2CH_2Cl$ or $CCl_3CHClCHCl_2$.

4. The process for the joint preparation of 1,3,3,3-tetrafluoropropene and 2,3,3,3-tetrafluoropropene according to claim 3, characterized in that, the starting material in step (a) comprises at least $CCl_2=CCl-CHCl_2$.

5. The process for the joint preparation of 1,3,3,3-tetrafluoropropene and 2,3,3,3-tetrafluoropropene according to claim 1, characterized in that, the fluorination catalyst described in step (a) is a Fe—Al—Mg—F compound catalyst in which the molar ratio of Fe, Al and Mg is (2-4):(1-2):(4-7); the preparation method of the catalyst comprises the following steps: dissolving soluble salts or alkoxides of the metals Fe, Al and Mg based on the molar ratio of corresponding alcohol solution under continuous stirring and ultrasonic conditions, adding a templating agent thereto, then adding a precipitant to carry out the reaction, performing precipitation, filtration and drying, and then calcining by stages at 100° C. to 250° C. under the conditions of not less than three temperature gradients, and then activating in hydrogen fluoride atmosphere at 200° C. to 300° C.

6. The process for the joint preparation of 1,3,3,3-tetrafluoropropene and 2,3,3,3-tetrafluoropropene according to claim 5, characterized in that, the molar ratio of Fe, Al and Mg in the Fe—Al—Mg—F compound catalyst in step (a) is 2:1:7; the templating agent in the preparation method is polyethylene glycol; the fluorination reaction conditions are as follows: the reaction temperature is 100° C. to 240° C.; the molar ratio of hydrogen fluoride to starting material is (5-20):1, and the contact time is 3-20 seconds.

7. The process for the joint preparation of 1,3,3,3-tetrafluoropropene and 2,3,3,3-tetrafluoropropene according to claim 1, characterized in that, the product stream in step (a) is introduced into a first rectification column for separation of hydrogen chloride, the product from the top of the column is hydrogen chloride which then enters an acid production system to give hydrochloric acid; the products from the bottom of the column are 1,2,3-trichloro-3,3-difluoropropylene, 1,2,3-trichloro-1,1,2-trifluoropropane, 1,2,3-trichloro-1,1,3-trifluoropropane and hydrogen fluoride, which enter a phase separator for phase separation; the phase separation temperature is −20° C. to 5° C., and the materials at the bottom of the phase separator, 1,2,3-trichloro-3,3-difluoropropene, 1,2,3-trichloro-1,1,2-trifluoropropane and 1,2,3-trichloro-1,1,3-trifluoropropane, are subjected to acid removal and drying before being dechlorinated as reaction materials of step (b).

8. The process for the joint preparation of 1,3,3,3-tetrafluoropropene and 2,3,3,3-tetrafluoropropene according to claim 1, characterized in that, the zero-valent transition metal in step (b) is Zn or Cu; the organic nitrogen-containing ligand is o-phenanthroline, 2,2-bipyridine, tris(2-pyridylmethyl)amine or tetramethyl ethylenediamine; and the reaction solvent is N,N-dimethylformamide or N-methylpyrrolidone.

9. The process for the joint preparation of 1,3,3,3-tetrafluoropropene and 2,3,3,3-tetrafluoropropene according to claim 1, characterized in that, the reaction conditions for the dechlorination reaction in step (b) are given as follows: the molar ratio of the reaction solvent to the total of 1,2,3-trichloro-3,3-difluoropropene, 1,2,3-trichloro-1,1,2-trifluoropropane and 1,2,3-trichloro-1,1,3-trifluoropropane is (5-20):1; the molar ratio of the zero-valent transition metal to the total of 1,2,3-trichloro-3,3-difluoropropene, 1,2,3-trichloro-1,1,2-trifluoropropane and 1,2,3-trichloro-1,1,3-trifluoropropane is (1-3):1; and the reaction temperature is 60° C. to 120° C.

10. The process for the joint preparation of 1,3,3,3-tetrafluoropropene and 2,3,3,3-tetrafluoropropene according to claim 1, characterized in that, the gas phase fluorination catalyst in step (c) is an Al—Co—Zn—F, in which the molar ratio of Al, Co and Zn is (6-8):(1-2):(1-2); the reaction conditions for the gas phase fluorination reaction are given as follows: the reaction temperature is 150° C. to 240° C., the molar ratio of hydrogen fluoride to the total of 3-chloro-3,3-difluoropropyne, 3-chloro-2,3,3-trifluoro propylene and 3-chloro-1,3,3-trifluoropropene is (5-20):1, and the contact time is 0.1-20 seconds.

11. The process for the joint preparation of 1,3,3,3-tetrafluoropropene and 2,3,3,3-tetrafluoropropene according to claim 5, characterized in that, the molar ratio of Fe, Al and Mg in the Fe—Al—Mg—F compound catalyst in step (a) is 2:1:7; the templating agent in the preparation method is polyethylene glycol; the fluorination reaction conditions are as follows: the reaction temperature is 100° C. to 240° C.; the molar ratio of hydrogen fluoride to starting material is (5-20):1, and the contact time is 3-20 seconds.

12. The process for the joint preparation of 1,3,3,3-tetrafluoropropene and 2,3,3,3-tetrafluoropropene according to claim 8, characterized in that, the reaction conditions for the dechlorination reaction in step (b) are given as follows: the molar ratio of the reaction solvent to the total of 1,2,3-trichloro-3,3-difluoropropene, 1,2,3-trichloro-1,1,2-trifluoropropane and 1,2,3-trichloro-1,1,3-trifluoropropane is (5-20):1; the molar ratio of the zero-valent transition metal to the total of 1,2,3-trichloro-3,3-difluoropropene, 1,2,3-trichloro-1,1,2-trifluoropropane and 1,2,3-trichloro-1,1,3-trifluoropropane is (1-3):1; and the reaction temperature is 60° C. to 120° C.

\* \* \* \* \*

UNITED STATES PATENT AND TRADEMARK OFFICE
CERTIFICATE OF CORRECTION

PATENT NO. : 9,873,649 B2
APPLICATION NO. : 15/535260
DATED : January 23, 2018
INVENTOR(S) : Jian Lv et al.

Page 1 of 1

It is certified that error appears in the above-identified patent and that said Letters Patent is hereby corrected as shown below:

In the Claims

Claim 2, Column 16, Line 50, replace "$CFCl_2CFCH_2Cl$" (first term) with "$CFCl_2CFClCH_2Cl$"

Signed and Sealed this
Eighth Day of May, 2018

Andrei Iancu
*Director of the United States Patent and Trademark Office*